US009737510B2

(12) United States Patent
Reddy et al.

(10) Patent No.: US 9,737,510 B2
(45) Date of Patent: Aug. 22, 2017

(54) INDAZOLE COMPOUNDS AND A PROCESS FOR THE PREPARATION THEREOF

(71) Applicants: Council of Scientific & Industrial Research, New Delhi (IN); Shantani Proteome Analytics Pvt. Ltd, Pune, Maharashtra (IN)

(72) Inventors: Dumbala Srinivasa Reddy, Maharashtra (IN); Chaitanya Saxena, Maharashtra (IN); Kashinath Komirishetty, Maharashtra (IN)

(73) Assignees: COUNCIL OF SCIENTIFIC & INDUSTRIAL RESEARCH, New Delhi (IN); SHANTANI PROTEOME ANALYTICS PVT. LTD, Pune (IN)

( * ) Notice: Subject to any disclaimer, the term of this patent is extended or adjusted under 35 U.S.C. 154(b) by 72 days.

(21) Appl. No.: 14/908,805

(22) PCT Filed: Jul. 31, 2014

(86) PCT No.: PCT/IN2014/000507
§ 371 (c)(1),
(2) Date: Jan. 29, 2016

(87) PCT Pub. No.: WO2015/015519
PCT Pub. Date: May 2, 2015

(65) Prior Publication Data
US 2016/0185759 A1    Jun. 30, 2016

(30) Foreign Application Priority Data
Jul. 31, 2013   (IN) ........................... 2296/DEL/2013

(51) Int. Cl.
*A61K 31/4184*   (2006.01)
*C07D 403/04*    (2006.01)

(52) U.S. Cl.
CPC ........ *A61K 31/4184* (2013.01); *C07D 403/04* (2013.01)

(58) Field of Classification Search
CPC .......................... A61K 31/4184; C07D 403/04
(Continued)

(56) References Cited

U.S. PATENT DOCUMENTS

2003/0109550 A1*   6/2003   Clare ................... C07D 231/56
                                                                    514/338
2004/0009976 A1    1/2004   Takeuchi et al.

OTHER PUBLICATIONS

International Preliminary Report on Patentability and Written Opinion of the International Searching Authority issued in PCT/IN2014/000507 dated Feb. 11, 2016.

* cited by examiner

*Primary Examiner* — Kamal Saeed
*Assistant Examiner* — Janet L Coppins
(74) *Attorney, Agent, or Firm* — Foley & Lardner LLP

(57) ABSTRACT

The patent discloses novel indazole compounds of general formula 1 and analogues thereof, use thereof for the treatment of diabetes, diabetic complications, cardiovascular dysfuntion or related diseases, pharmaceutical compositions comprising them and processes for their preparation.

(Continued)

a b c

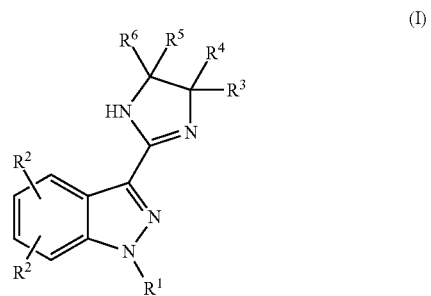
(I)
7 Claims, 10 Drawing Sheets
(58) Field of Classification Search
USPC .................................. 514/393; 548/312.4
See application file for complete search history.

a b a b a b

INDAZOLE COMPOUNDS AND A PROCESS FOR THE PREPARATION THEREOF

FIELD OF THE INVENTION

This invention relates to novel indazole compounds of general formula 1 and a process for the preparation thereof. The invention specifically relates to novel indazole compounds, derivatives thereof and process for synthesizing the same. Further the invention relates to of use of novel indazole of general formula 1 for the treatment of diabetes, diabetic complications, metabolic disorders, cardiovascular dysfunction including hypertension, auto-immune and inflammation related disorders or diseases where impaired glucose disposal and imbalance energy expenditure between fatty acid and glucose pathway is present and also to pharmaceutical compositions comprising them.

BACKGROUND AND PRIOR ART OF THE INVENTION

Type 2 diabetes mellitus (T2DM) is one of the most common, chronic, and life threatening diseases. Every year, the prevalence of T2DM is increasing worldwide and recently, World Health Organization (WHO) predicted that by 2030, the number of patients diagnosed with T2DM will be more than 366 millions. Clinically T2DM is characterized by increased blood glucose levels, either because of defect in insulin secretion, insulin resistance or both.

US 2004/0009976 A1 discloses a compound of Formula (A1):

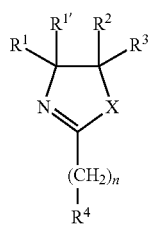

and their use for the treatment of Type II diabetes and stimulating insulin secretion in mammals. US 2003/0109550 A1 discloses a compound of formula A2,

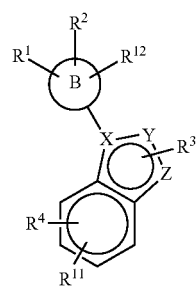

wherein, B is a 5 or 6 saturated or unsaturated heterocyclic wherein said heterocyclic is optionally substituted with $R^1$, $R^2$, and R12; X is selected from the group consisting of: N and C; Y and Z are independently selected from the group consisting of: N, CH, $CR^3$, S, and O; $R^3$ is selected from the group consisting of: substituted or unsubstituted amidine, alkylamino, aminoalkyl, $CONHR^7$, $NH_2$, $NHCOR^6$, and $CH_2NHCOR^6$.

EP 0418845 B1 discloses novel Pyrazole derivatives, processes for preparation thereof and pharmaceutical composition comprising the same. It provides a compound of the formula A3:

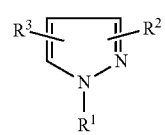

Wherein, R1 is aryl which may be substituted with substituent(s) selected from the group consisting of 40 lower alkyl, halogen, lower alkoxy, lower alkylthio, lower alkylsulfinyl, lower alkylsulfonyl, hydroxy, lower alkylsulfonyloxy, nitro, amino, lower alkylamino, acylamino and lower alkyl-(acyl)amino; or a heterocyclic group; R2 is hydrogen; methyl substituted with amino, lower alkylamino, halogen or acyloxy; acyl; 45 acylamino; cyano; halogen; lower alkylthio; lower alkylsulfinyl; or a heterocyclic group; and R3 is aryl substituted with lower alkyl, lower alkylthio, lower alkylsulfinyl, halogen, amino, lower alkylamino, acylamino, lower alkyl(acyl)amino, lower alkoxy, cyano, hydroxy or acyl; or a heterocyclic group which may be substituted with lower alkylthio, lower alkylsulfinyl or 50 lower alkylsulfonyl.

U.S. Pat. No. 4,436,913 discloses 1H- and 2H-indazole derivatives and pharmaceuticals containing these blood-pressure lowering 1H- and 2H indazole derivatives of the formula A4,

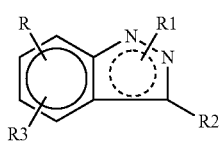

and their acid addition salts, wherein R1 may be in position 1 or position 2 on the nitrogen atoms in formula 1. The groups R1, R2 and R3 represent hydrogen or the usual lower molecular groups. The R group is a 2 imidazolinylamino group or a 3,4,5,6-tetryhydropyrimidinylamino group, wherein these groups may also be present in their tautomeric forms. These groups may also be in an aryl group in the R1 group, in which case the R group may also be a halogen atom. R may only represent one of the heterocyclic secondary or tertiary amino groups in the 4 or 7th position for the 1H indazole derivatives when the R1 group is simultaneously an aryl or an aralkyl group. U.S. Pat. No. 6,878,735 B2 discloses an imidazoline of the formula A5,

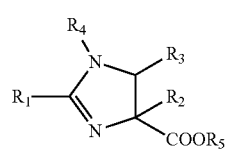

Wherein R1 is aryl, optionally substituted, R2 is selected from the group consisting of alkyl, acyl, aryl, aralkyl, heteroaryl containing 5 to 14 ring members, and heterocyclic containing 5 to 12 ring members; R3 is aryl, optionally substituted, R4 is aralkyl, optionally substituted, and R5 is selected from the group consisting of hydrogen and an alkyl group, all of Which are optionally substituted.

U.S. Pat. No. 7,541,376 B2 provides a novel 1H-indazole compound having an excellent JNK inhibitory action. More specifically, it provides a compound represented by the formula A6,

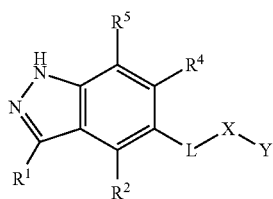

A6

Wherein $R^1$ is a $C_6$-$C_{14}$ aromatic cyclic hydrocarbon group etc.; $R^2$, W and $R^5$ each independently represent a hydrogen atom, a halogen atom, a cyano group etc.; L is a single bond, or a $C_1$-$C_6$ alkylene group etc.; X is a single bond, or a group represented by —CO—NH— or —NH—, CO—, etc.; and Y is a $C_3$-$C_8$ cycloalkyl group, a $C_6$-$C_{14}$ aromatic cyclic hydrocarbon group or a 5- to 14-membered aromatic heterocyclic group etc., a salt thereof or a hydrate of them.

US 2011/0034441 A1 discloses a compound of formula A7,

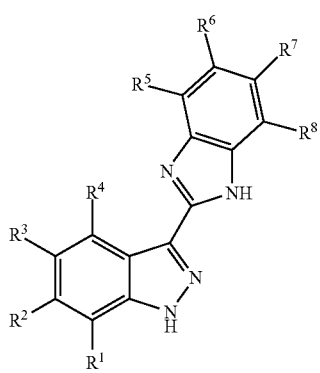

A7 wherein $R^1$, $R^2$, $R^4$, $R^5$, $R^6$, W and $R^8$ are independently selected from the group consisting of H, $C_{1-9}$ alkyl, halide, —$CF_3$, —($C_{1-9}$ alkyl)$_n$carbocyclyl$R^{12}$, —($C_{1-9}$ alkyl)$_n$heterocyclyl$R^{12}$, —($C_{1-9}$ alkyl)$_n$aryl$R^{12}$, —($C_{1-9}$ alkyl)$_n$heteroaryl$R^{12}$, —($C_{1-9}$ alkyl)$_n$OR$^9$, —($C_{1-9}$ alkyl)$_n$SR$^9$, —($C_{1-9}$ alkyl)$_n$S(=O)$R^{10}$, —($C_{1-9}$ alkyl)$_n$SO$_2$R$^9$, —($C_{1-9}$ alkyl)$_n$N(R$^9$)S(=O)$R^{10}$, —($C_{1-9}$ alkyl)$_n$N(R$^9$)SO$_2$R$^9$, —($C_{1-9}$ alkyl)$_n$SO$_2$N(R$^9$)$_2$, —($C_{1-9}$ alkyl)$_n$N(R$^9$)$_2$, —($C_{1-9}$ alkyl)$_n$N(R$^9$)C(=A)N(R$^9$)$_2$, —($C_{1-9}$ alkyl)$_n$NR$^9$C(=O)OR$^9$, —($C_{1-9}$ alkyl)$_n$C(=A)N(R$^9$)$_2$, —($C_{1-9}$ alkyl)$_n$N(R$^9$)C(=A)R$^9$, —($C_{1-9}$ alkyl)$_n$OC(=O)N(R$^9$)$_2$, —NO$_2$, —CN, —($C_{1-9}$ alkyl)$_n$CO$_2$R$^9$ and —($C_{1-9}$ alkyl)$_n$C(=A)R$^9$.

US 2002/0161022 A1 discloses a compound of formula A8,

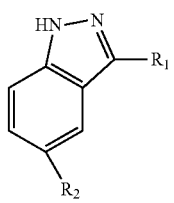

A8

Wherein R1 is a substituted or unsubstituted alkyl, aryl, heteroaryl, carbocycle, heterocycle etc.; R2 is a substituted or unsubstituted alkyl, aryl, heteroaryl, carbocycle, heterocycle etc.

WO2011057959 discloses a compound of formula A9,

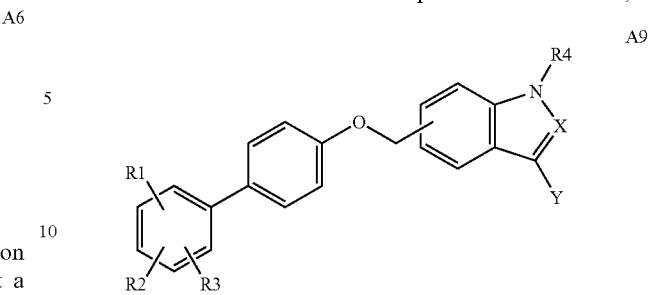

A9 wherein, R1, R2, R3, independently of each other; is hydrogen, halogen, lower alkyl or alkoxy; R4 is hydrogen, unsubstituted lower alkyl, or lower alkyl substituted with one to four substituents independently selected from the group consisting of methyl, (=0) and —COOH; X is CH or N; and Y is hydrogen or —NH$_2$, or a pharmaceutically acceptable salt thereof. Further, it relates to the use of compound A9, or a pharmaceutically acceptable salt thereof, for the treatment or prophylaxis of metabolic diseases and disorders.

Article titled, "2-(4,5-Dihydro-1H-imidazol-2-yl)indazole (indazim) derivatives as selective I2 imidazoline receptor ligands" by F. Saczewski et al. in European Journal of Pharmaceutical Sciences 20 (2003) 201-208 reports the synthesis of a series of variously substituted 2-(4,5-dihydro-1H-imidazol-2-yl)indazoles and 2-(4,5-dihydro-1H-imidazol-2-yl)-4,5,6,7-tetrahydroindazole. Further, it reports that 4-Chloro-2-(4,5-dihydro-1H-imidazol-2-yl)indazole (3f, 4-Cl-indazim) which shows good affinity at imidazoline I2 receptor and unprecedented among this type of imidazoline ligands low affinity at alpha-2-adrenoceptor.

Article titled, "Click" synthesis of small molecule-peptide conjugates for organelle-specific delivery and inhibition of lysosomal cysteine proteases" By YuhuiLoh in ChemCommun (Camb). 2010 Nov. 28; 46 (44):8407-9 reports a click chemistry approach for the synthesis of small molecule inhibitor-peptide conjugates to achieve organelle-specific delivery. It further provides a process where COOH group was converted to —CONNH2ME using N-methylmorpholine (NMM) isobutyl chloroformate (ISCF) and Methylhydrazine salt.

Article, "Carboxylic Compounds, Nitriles, and Their Interconversion" in Organic Mechanisms, 2010, pp 321-338 reports Trifluoroacetic acid anhydride-mediated dehydration of pivalic acid amide (A) to pivalic acid nitrile (B) with the reagent forming trifluoroacetic acid $F_3C$—$CO_2H$.

Article titled, "Synthesis and antidiabetic activity of 2,5-disubstituted-3-imidazol-2-yl-pyrrolo[2,3-b]pyridines and thieno[2,3-b]pyridines" by Rajesh H. Bahekar, Mukul R. Jain, Pradip A. Jadav, Vijay M. Prajapati, Dipam N. Patel, Arun A. Gupta, Ajay Sharma, Robby Tom, Debdutta Bandyopadhya, Honey Modi and Pankaj. R. Patel in Bioorganic & Medicinal Chemistry 15 (2007) 6782-6795 reports the conversion of nitriles to imidazoline using ethylene diamine, $P_2S_5$ at 120° C. and 5 hrs.

The drugs used in the diabetes therapy belong to the following therapeutic classes, defined on the basis of the pathogenetic role of the insulin resistance (Trends in Pharm. Sci. 21, 259-265 2000): insulin, sulphonylureas, metformin, inhibitors of alpha-glycosidase (acarbose) and thiazolidinediones (troglitazone). Insulin is the most known drug and it is considered the reference drug in diabetes treatment. But, insulin therapy suffers from the following drawbacks: the drug is administrable only by parenteral route, it is necessary to constantly control the glycaemia levels, local allergic reactions can arise, insulin resistance compels to meaningfully increase the drug dosage during the time, the local tolerability is poor.

Also the other therapeutical approaches are not without drawbacks, sometimes even remarkable. For example sulphonylureas, which are administered alone or in combination with insulin or with other oral hypoglycemizing drugs, can cause hypoglycemia. Metformin, which is used alone or in combination with sulphonylurea, is contraindicated in the presence of renal and hepatic diseases, and can induce a state of lactic acidosis. Acarbose is used alone or in combination with sulphonylurea for reducing the postprandial glycemic levels, but it often induces side effects at the gastrointestinal system level. Troglitazone, which is only used in combination with insulin, can induce hepatotoxic effects.

Thus, there is an urgent need to develop some novel therapeutic approaches for glycemic control that can attempt to preserve normal physiological response to meal intake. One such approach is based on the development of insulin secretagogues, which do not cause glucose secretion under basal blood glucose levels but show only glucose-dependent insulin release.

Considering the standing problems in the prior art and long felt need of a new drug which shows glucose dependent insulin release, overcoming side-effects for treatment of diabetes or diabetes related complications inventors have come up with the current invention. The current invention discloses novel indazole compounds, derivatives thereof and method to synthesize the same. The compounds show anti diabetic activity against both type 1 and type 2 diabetes and related complications like diabetic neuropathy, diabetic retinopathy and a variety of vascular diseases which are results of continued fluctuating glucose blood levels.

OBJECTIVES OF THE INVENTION

The main object of the invention is to provide novel indazole compounds of general formula 1.

Another objective of the invention is to provide a process to synthesize the compounds of Formula 1.

Yet another objective of the invention is to provide pharmaceutical compositions of the compounds for treating diabetes, diabetes related complications and hypertension.

Yet another objective of the invention is to provide use of novel indazole of general formula 1 for the treatment of diabetes, diabetic complications, metabolic disorders, cardiovascular dysfunction including hypertension, auto-immune and inflammation related disorders or diseases where impaired glucose disposal and imbalance energy expenditure between fatty acid and glucose pathway and associated triglyceride level is present.

SUMMARY OF THE INVENTION

Accordingly, the present invention provides Indazole compounds of formula 1,

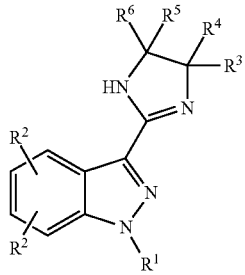

Formula 1

Wherein:
$R^1$ are hydrogen or alkyl oraryl or heteroaryl;
$R^2$ are H or halogen
$R^3$, $R^4$, $R^5$, and $R^6$ are independently hydrogen or alkyl, aryl, hetero aryl;
any two adjacent groups selected from $R_3$, $R_4$, $R_5$, and $R_6$ may form a 3-8 membered cycle which may additionally contain hetero atoms; and their
analogues, positional isomers, stereoisomers, derivatives, and pharmaceutically acceptable salt thereof.

In one embodiment of the present invention Indazole compounds of formula 1 are represented by following compounds
a. 5-Chloro-3-(4,5-dihydro-1H-imidazol-2-yl)-1H-indazole;
b. 5-Chloro-3-(4,5-dihydro-1H-imidazol-2-yl)-1-methyl-3a,7a-dihydro-1H-indazole;
c. 5-chloro-3-(3a,4,5,6,7,7a-hexahydro-1H-benzo[d]imidazol-2-yl)-1H-indazole;
d. 5-Chloro-3-(4,5-dihydro-1H-imidazol-2-yl)-1-ethyl-1H-indazole;
e. 1-Benzyl-5-chloro-3-(4,5-dihydro-1H-imidazol-2-yl)-1H-indazole;
f. 3-(4,5-dihydro-1H-imidazol-2-yl)-1H-indazole;
g. 3-(4,5-dihydro-1H-imidazol-2-yl)-1-methyl-1H-indazole;
h. 3-(3a,4,5,6,7,7a-hexahydro-1H-benzo[d]imidazol-2-yl)-1H-indazole.

In an embodiment of the present invention a process for the preparation of Indazole compounds of formula, wherein the said process comprising the steps of;
i. converting 5-Chloro isatin (1) into 5-chloro indazole 3-carboxylic acid (2);
ii. treating the compound 5-chloro indazole 3-carboxylic acid (2) with isobutyl chloroformate and N-methylmorpholine under argon followed by reaction with aq. ammonia to obtain 5-chloro-1H-indazole-3-carboxamide (3);
iii. treating the compound 5-chloro-1H-indazole-3-carboxamide (3) with pyridine and trifluroacetic anhydride to obtain cyano compound (4);
iv. reacting cyano compound (4) with potassium carbonate and alkyl halide in a solvent selected from acetone to obtain substituted indazole carbonitrile;
v. reacting substituted indazole carbonitrile with diamine in presence of $P_2S_5$ to obtain compounds of general formula 1

In another embodiment of the present invention alkyl halide used in step (iv) is selected from the group consisting of ethyl bromide, methyl iodide, benzyl bromide.

In another embodiment of the present invention diamine used in step (v) is selected from the group consisting of 1,2-Cyclohexanediamine, ethylene diamine.

In another embodiment of the present invention a pharmaceutical formulation comprising compound of Formula 1 as an active ingredient, or their analogues, positional isomers, stereoisomers, derivatives, and pharmaceutically acceptable salt thereof, together with one or more pharmaceutically acceptable carriers, diluents or excipients.

In another embodiment of the present invention Indazole compounds of formula 1 are useful for treatment of diabetes, diabetic complications, metabolic disorders, cardiovascular dysfunctions or related diseases where impaired glucose disposal, altered triglyceride levels or reduced beta-cell functions is present.

In another, embodiment of the present invention Indazole compounds of formula 1, wherein it administered to mammal a therapeutically effective amount of a compound of Formula 1, or their analogues, positional isomers, stereoisomers, derivatives, and pharmaceutically acceptable salt.

DETAILED DESCRIPTION OF THE INVENTION

Figure 1:
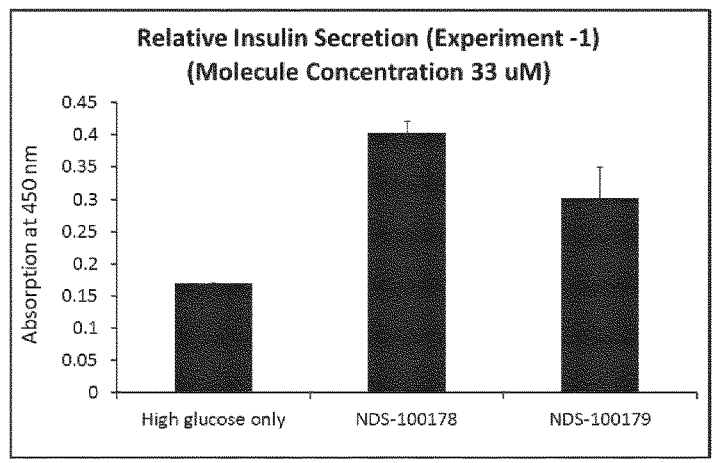
FIG. 1: depicts Insulin secretion ability of NDS100178 and NDS100179 on three different days.
Figure 1:
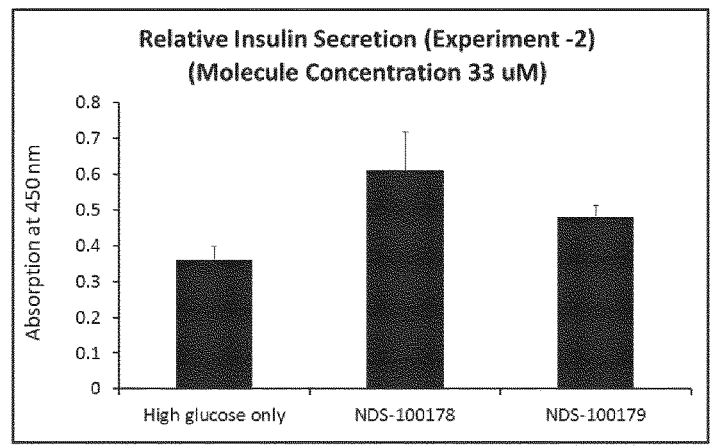
Figure 1:
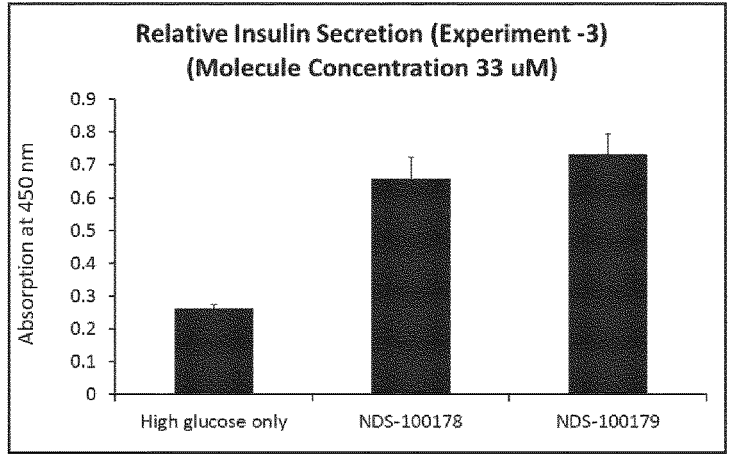

This invention relates novel indazole compounds of general formula 1 and a process for the preparation thereof. The present invention provides novel compounds and its analogues, positional isomers, stereoisomers, derivatives and pharmaceutically acceptable salt thereof of Indazole compounds of general formula 1

Formula 1

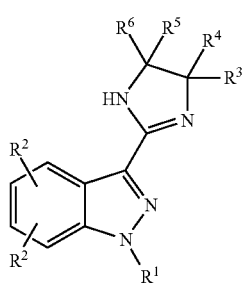

Wherein:
$R^1$ are hydrogen or alkyl oraryl or heteroaryl;
$R^2$ are H or halogen
$R^3$, $R^4$, $R^5$ and $R^6$ are independently hydrogen or alkyl, aryl, hetero aryl; Any two adjacent groups selected from $R^3$, $R^4$, $R^5$ and $R^6$ may form a 3-8 membered cycle which may additionally contain hetero atoms;
and their analogues, positional isomers, stereoisomers, derivatives, and pharmaceutically acceptable salt thereof.

In a preferred embodiment, the present invention provides a compound of formula 1 selected from the group of:
5-Chloro-3-(4,5-dihydro-1H-imidazol-2-yl)-1H-indazole (NDS100178);
5-Chloro-3-(4,5-dihydro-1H-imidazol-2-yl)-1-methyl-3a,7a-dihydro-1H-indazole (7, NDS100179);
5-chloro-3-(3a,4,5,6,7,7a-hexahydro-1H-benzo[d]imidazol-2-yl)-1H-indazole (8, NDS100281);
5-Chloro-3-(4,5-dihydro-1H-imidazol-2-yl)-1-ethyl-1H-indazole (10, NDS100282);
1-Benzyl-5-chloro-3-(4,5-dihydro-1H-imidazol-2-yl)-1H-indazole 12 (NDS100283);
3-(4,5-dihydro-1H-imidazol-2-yl)-1H-indazole (16, NDS100277);
3-(4,5-dihydro-1H-imidazol-2-yl)-1-methyl-1H-indazole 18 (NDS100278);
3-(3a,4,5,6,7,7a-hexahydro-1H-benzo[d]imidazol-2-yl)-1H-indazole (19, NDS100279).

In another embodiment, the present invention provides a process for preparation of novel compounds of general formula 1 from isatin compound of formula II,

II

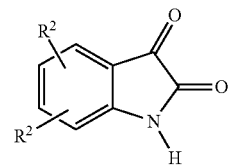

Wherein $R^2$ are H or halogen;
Comprising the steps of:
Converting isatin compound of formula (II) into carboxylic acid;
Treating the carboxylic acid compound step (a) with isobutyl chloroformate and N-methylmorpholine followed by reaction with aq. ammonia to obtain amide;
Treating the amide compound of step (b) with pyridine and trifluroacetic anhydride to furnish cyano compound;
Reacting cyano compound of step (c) with diamine in presence of $P_2S_5$ to give desired compound of formula (1).

In a preferred embodiment, the present invention provides a process for preparation of novel compounds of formula 5, comprising:
Converting 5-Chloro isatin (1) into 5-chloro indazole 3-carboxylic acid (2);
Converting the compound (2) of step (a) into amide (3);
Treating amide 3 of step (b) with pyridine and trifluroacetic anhydride to furnish cyano compound (4);
Reacting compound (4) of step (c) with ethylene diamine in presence of $P_2S_5$ to give compound (5).

The process for the preparation of compound 5 is depicted in scheme 1.

Scheme: 1

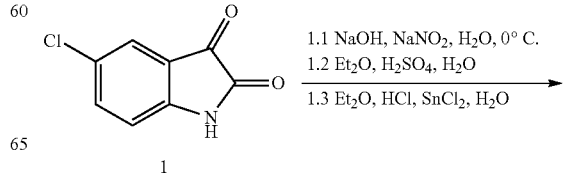

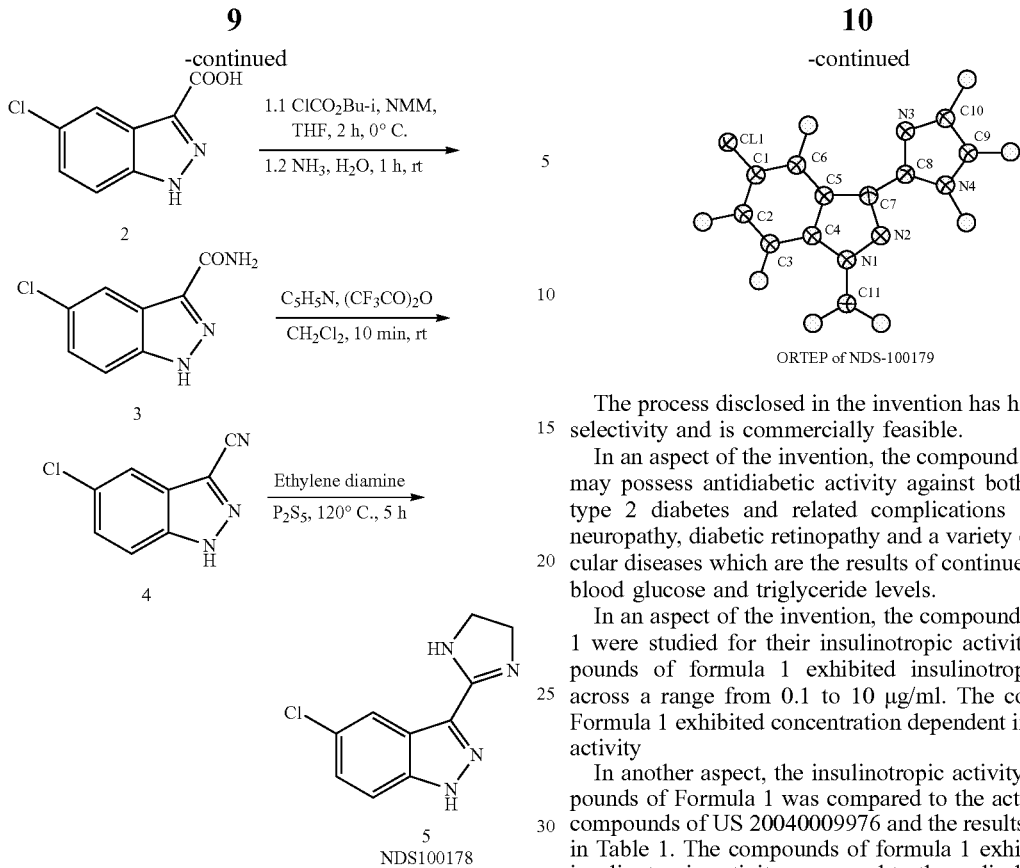

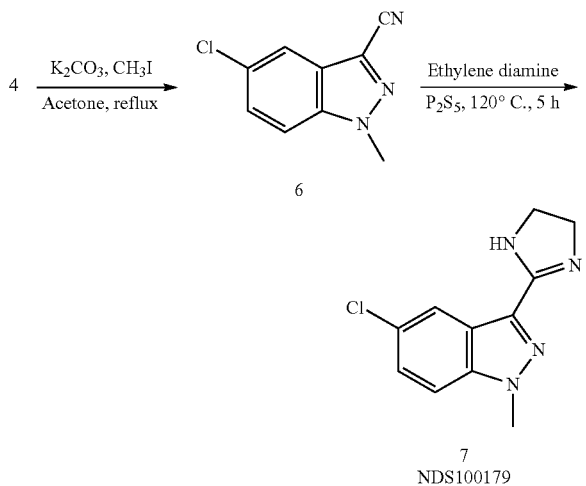

ORTEP of NDS-100179

The process disclosed in the invention has high yield and selectivity and is commercially feasible.

In an aspect of the invention, the compound of formula 1 may possess antidiabetic activity against both type 1 and type 2 diabetes and related complications like diabetic neuropathy, diabetic retinopathy and a variety of cardiovascular diseases which are the results of continued fluctuating blood glucose and triglyceride levels.

In an aspect of the invention, the compounds of Formula 1 were studied for their insulinotropic activity. The compounds of formula 1 exhibited insulinotropic activities across a range from 0.1 to 10 µg/ml. The compounds of Formula 1 exhibited concentration dependent insulinotropic activity In another aspect, the insulinotropic activity of the compounds of Formula 1 was compared to the activity of prior compounds of US 20040009976 and the results are as listed in Table 1. The compounds of formula 1 exhibit enhanced insulinotropic activity compared to those disclosed in prior arts.

In yet another aspect, the inventors studied the glucose concentration dependent insulin secretion or glucose stimulated insulin secretion (GSIS) in several models. The study was conducted in human islets, C57BL Mice and MIN 6 cells. The compounds of formula 1 induce GSIS and this is evident by referring to FIG. 5. The test further confirms that the GSIS effect of the compounds of the invention are independent of the biological system and their make-up.

Figure 6:
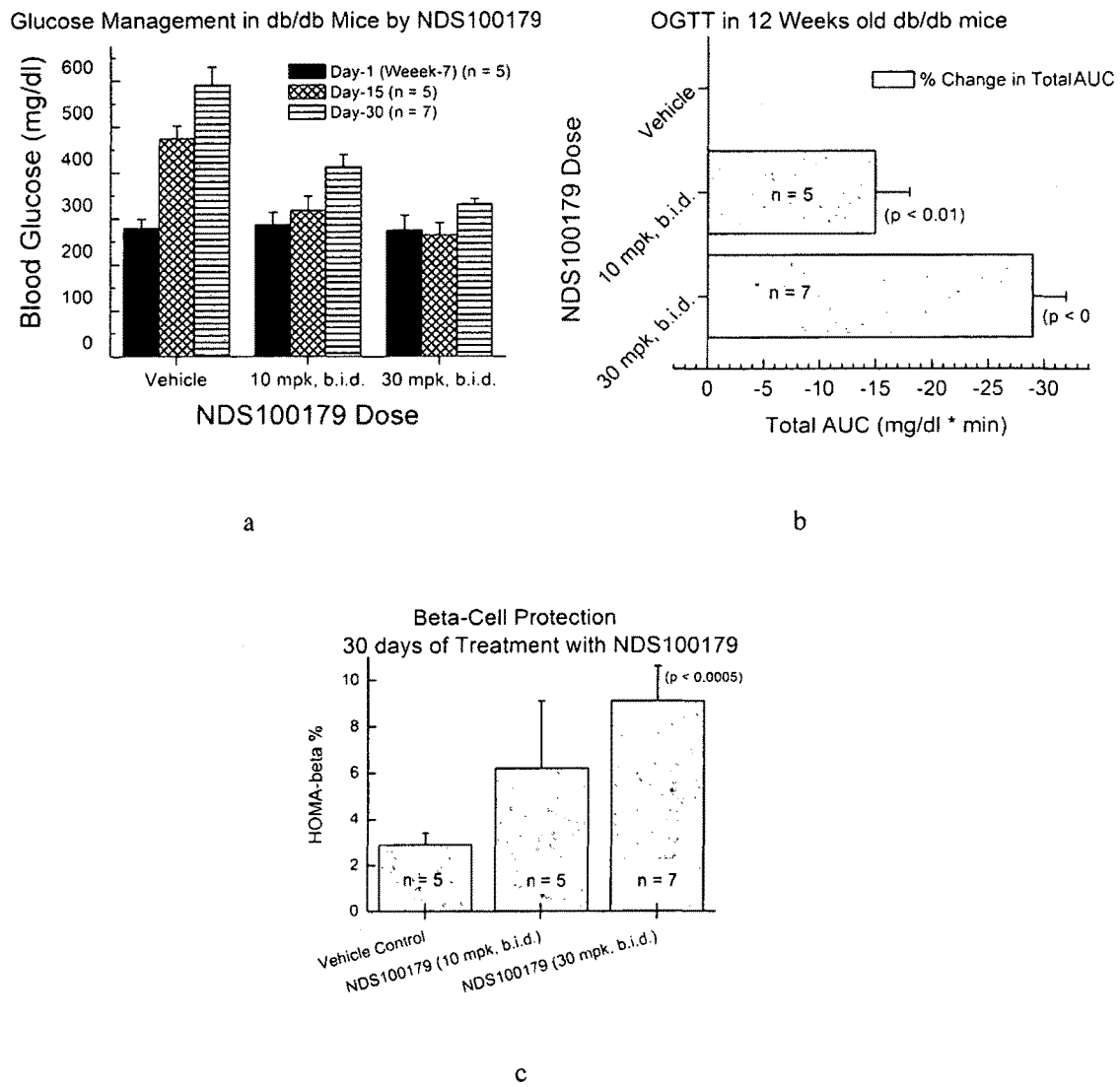
FIG. 6: depicts a) Glycaemic Control in NDS100179 Treated db/db Mice; b) Glucose Tolerance in NDS100179 Treated db/db Mice; c) Body Weight Measurements of Control or NDS100179 Treated db/db Mice.

Further in the studies compound of Formula 1 provided excellent control on increasing fasted blood glucose levels and improved glucose tolerance in OGTT tests in animal model of diabetes (db/db mice) when animals were treated for 30 days with the compound. This provides a direct indication of the anti-diabetic properties of compound of Formula 1 (FIGS. 6a and 6b). Also beta cell functions were better preserved/restored in compound treated animal confirms additional benefit of the compound (FIG. 6c)

Figure 7:
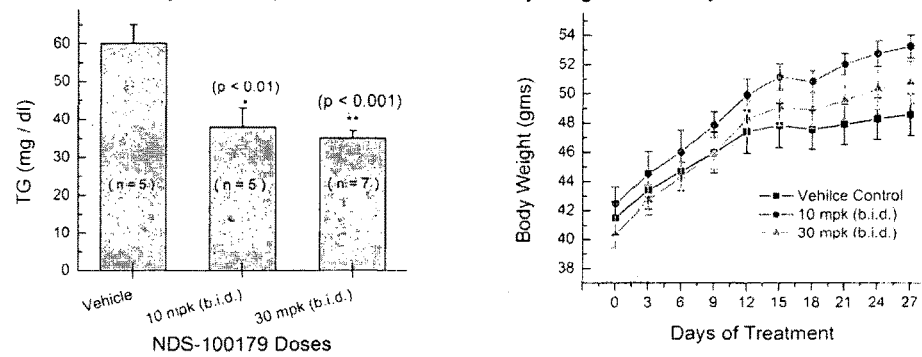
FIG. 7: depicts a) Triglyceride Measurements in Control or NDS100179 Treated db/db Mice; b) Beta-cell Function Measurements in Control or NDS100179 Treated db/db Mice.

In yet another finding compound of Formula 1 decreased triglyceride levels in animal model of diabetes (db/db mice) when animals were treated for 30 days with the compound (FIG. 7). Low triglyceride levels are linked with improved cardiac health and compound provided significant therapeutic cardio-vascular benefits.

Figure 8:
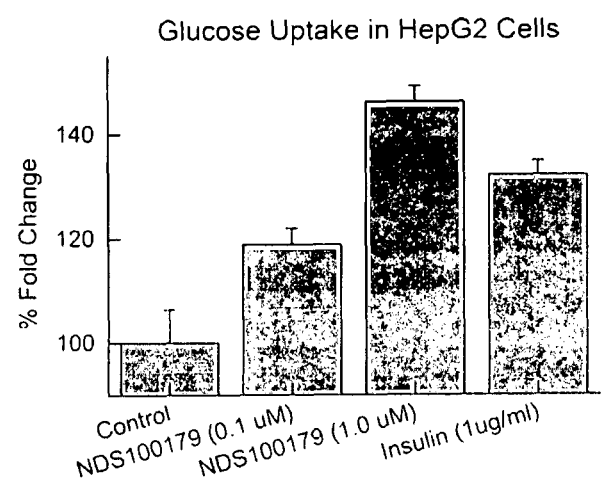
FIG. 8: depicts Glucose uptake in HepG2 cells.

Referring to FIG. 8, the glucose uptake by HepG2 cells was in presence of the compound was studied. Glucose uptake by HepG2 cells represents a model of studying glucose uptake by the liver cells. Increased glucose uptake is characterized as improved insulin sensitivity and compounds that can stimulate glucose uptake and improve insulin sensitivity are useful in management of type 2 diabetes as they eventually help in maintaining glucose homeostasis by decreasing glucose from the circulating system. As evident compound increases glucose uptake in HepG2 cells and hence represent a compound that can help in maintaining glucose homeostasis and managing type 2 diabetes.

In another preferred embodiment, the present invention provides a process for preparation of novel compounds of formula 7, said process comprising:

Converting 5-Chloro isatin (1) into 5-chloro indazole 3-carboxylic acid (2);
Converting the compound (2) of step (a) into amide (3);
Treatingamide 3 of step (b) with pyridine and trifluroacetic anhydride to furnish cyano compound (4);
Methylating compound (4) of step (c) to obtain compound (6),
Reacting compound (6) of step (c) with ethylene diamine in presence of $P_2S_5$ to give compound (7).

The process for the preparation of compound 7 is depicted in scheme 2:

Scheme: 2

In yet another aspect, the mechanism of action of the compounds of formula 1 is proposed by the inventors. Working through imidazoline receptor compound increases Diacylglycerol and downstream Arachidonic Acids in the cell. Arachidonic Acid metabolites are involved in insulin exocytosis. A novel finding that inhibiting LTA4H, an enzyme that can maintain the pool of Arachidonic Acid in the cell, can enhance insulin secretion has been established by the inventors. NDS100178 inhibits LTA4H (1050<500 nM) while the IC50 against LTA4H target of example 6 from patent US20040009976 Compound: 5-Chloro-2-methyl-3-(4,5-dihydro-1-H-imidazol-2-yl)-1H-indole) is above 10 uM.

In yet another embodiment, a pharmaceutical composition is provided comprising a compound of formula (I), or a stereoisomer, or ester or pharmaceutically acceptable salt thereof, and a pharmaceutically acceptable carrier, diluent or excipient.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, In still another embodiment, the present invention relates to administering 'an effective amount' of the 'composition of invention' to a subject suffering from said disease. Accordingly, compound of formula 1, pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

In conclusion it may be stated that, the compounds of formula 1 provide a novel alternative to diabetics and subjects suffering from its complications thereof by inducing GSIS, managing blood glucose concentrations proportionate to subject's body weight and concentration administered, improving cardiovascular safety profile with decrease in triglycerides and restoring/preserving beta-cell functions.

The following examples are given by way of illustration of the working of the invention in actual practice and should not be construed to limit the scope of the present invention in any way.

EXAMPLES

Example: 1

5-Chloro-3-(4,5-dihydro-1H-imidazol-2-yl)-1H-indazole (NDS100178)

5-chloro-1H-indazole-3-carboxamide (3)

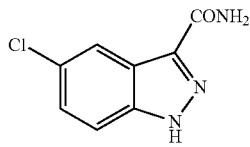

To a solution of 5-chloro indazole 3-carboxylic acid[1] 2 (0.8 g, 4.0 mmol) in anhydrous THF (20 mL) was added isobutyl chloroformate (0.64 mL, 4.9 mmol) and N-methylmorpholine (0.7 mL, 6.1 mmol) under argon at 0° C. and the mixture was stirred for 2 h. Then to this mixture 10 mL of aqueous $NH_3$ was added and mixture was stirred at 25° C. for 1 h. THF was removed under reduced pressure solid was obtained filtered through buchner funnel, solid was washed with diethyl ether and dried under vacuum to afford title compound 3 (0.5 g, 63%) as a pale yellow solid. IR $v_{max}$(film): $cm^{-1}$ 2925, 2854, 1463; $^1$H NMR (200 MHz, DMSO-$d_6$): δ 8.14 (d, J=1.6 Hz, 1H), 7.80 (b s, 1H), 7.66 (d, J=8.9 Hz, 1H), 7.45-7.39 (m, 2H); MS: 218 (M+Na)$^+$.

5-chloro-1H-indazole-3-carbonitrile (4)

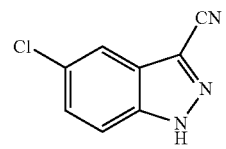

5-chloro-1H-indazole-3-carboxamide 3 (0.60 g, 3.0 mmol) was dissolved in pyridine (6 mL) and dry dichloromethane (6 mL). Trifluoroacetic acid anyhydride (1.0 mL, 7.7 mmol) was added and the reaction stirred at 25° C. for 10 minutes. The reaction mixture was concentrated in vacuo and the residue taken up in ethyl acetate, then washed with water, saturated sodium bicarbonate and brine. The organic phase was dried over sodium sulphate, filtered and concentrated to give the title compound 5-chloro-1H-indazole-3-carbonitrile 4 (0.5 g, 92%) as a pale yellow solid. IR $v_{max}$(film): $cm^{-1}$ 2233; $^1$H NMR (200 MHz, CDCl$_3$): δ 8.03 (d, J=9.1 Hz, I H), 7.96 (d, J=1.8 Hz, 1H), 7.75 (dd, J=9.1, 1.8 Hz, 1H).

5-Chloro-3-(4,5-dihydro-1H-imidazol-2-yl)-1H-indazole (5, NDS100178)

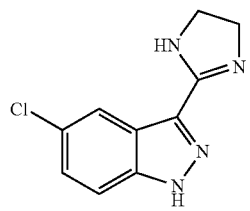

NDS100178

A mixture of 5-chloro-1H-indazole-3-carbonitrile 4 (0.2 g, 1.1 mmol), ethylene diamine (EDA, 4 mL), and $P_2S_5$ (0.1 g, 0.4 mmol) was heated at 120° C. for 5 h. The reaction mixture was poured into ice solid was obtained, filtered through Buchner funnel washed with diethyl ether and dried under vacuum to afford 5-Chloro-3-(4,5-dihydro-1H-imidazol-2-yl)-1H-indazole compound 5 NDS100178 (0.12 g, 49%) as off white solid. Mp=248-249° C.; $^1$H NMR (200 MHz, DMSO-$d_6$): δ 8.19 (s, 1H), 7.63 (d, J=8.9 Hz, 1H), 7.36 (d, J=8.9 Hz, 1H), 3.66 (bs, 4H); MS: 221 (M+H)$^+$.

Example: 2

5-Chloro-3-(4,5-dihydro-1H-imidazol-2-yl)-2-methyl-2H-indazole (NDS100179)

5-Chloro-1-methyl-1H-indazole-3-carbonitrile (6)

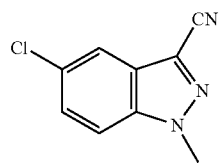

6

Potassium carbonate (0.23 g; 1.6 mmol) and methyl iodide (0.1 mL; 1.6 mmol) were added to a suspension of 5-chloro-1H-indazole-3-carbonitrile 4 (0.1 g; 0.5 mmol) in acetone (10 mL). The reaction mixture was heated at 65° C. for 4 h, cooled and filtered. The filtrate was concentrated under reduced pressure and purified by column chromatography (silica gel 100-200 mesh, 3:7 Ethyl acetate: Pet ether) to afford 5-Chloro-1-methyl-1H-indazole-3-carbonitrile 6(0.8 g, 75%) as a white solid. Mp=154-155° C.; $^1$H NMR (200 MHz, DMSO-$d_6$): δ 8.03 (d, J=1.9 Hz, 1H), 7.96 (d, J=8.9 Hz, 1H), 7.63 (dd, J=8.9, 1.9 Hz, 1H), 4.20 (s, 3H).

5-Chloro-3-(4,5-dihydro-1H-imidazol-2-yl)-1-methyl-3a,7a-dihydro-1H-indazole (7, NDS100179)

A mixture of 5-Chloro-1-methyl-1H-indazole-3-carbonitrile 6 (0.1 g, 1.0 mmol), EDA (4 mL), and $P_2S_5$ (0.046 g, 0.4 mmol) was heated at 120° C. for 5 h. The reaction mixture was poured into ice solid was obtained, filtered through Buchner funnel washed with diethyl ether and dried under vacuum to afford compound 7 (NDS100179) (0.060 g, 50%) as a white solid. Mp=174-175° C.; $^1$H NMR (200 MHz, DMSO-$d_6$): δ 8.21 (d, J=2.0 Hz, 1H), 7.77 (d, J=8.8 Hz, 1H), 7.47 (dd, J=8.8, 2.0 Hz, 1H), 6.84 (bs, 1H), 4.11 (s, 3H), 3.62 (bs, 4H). $^{13}$C NMR (100 MHz, DMSO-$d_6$) δ=160.1, 139.6, 132.0, 128.2, 127.2, 122.4, 120.1, 111.2, 35.2; MS; 235 (M+H)+.

Example: 3

5-chloro-3-(3a,4,5,6,7,7a-hexahydro-1H-benzo[d]imidazol-2-yl)-1H-indazole (NDS100281)

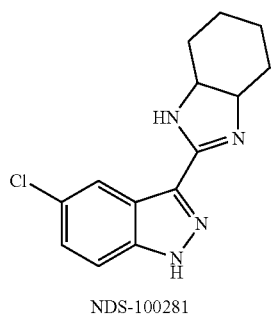

8

NDS-100281

A mixture of 5-chloro-1H-indazole-3-carbonitrile 4 (0.1 g, 0.5 mmol), 1,2-Cyclohexanediamine (2 mL), and $P_2S_5$ (0.05 g, 0.2 mmol) was heated at 120° C. for 5 h. The reaction mixture was poured into ice solid was obtained, filtered through Buchner funnel washed with diethyl ether and dried under vacuum to afford 5-chloro-3-(3a,4,5,6,7,7a-hexahydro-1H-benzo[d]imidazol-2-yl)-1H-indazole NDS100281 (60 mg, 40%) as pale yellow solid. $^1$H NMR (200 MHz, CD$_3$OD) δ=8.08 (d, J=1.6 Hz, 1H), 7.51 (d, J=8.8 Hz, 1H), 7.23 (dd, J=2.0, 8.9 Hz, 1H), 3.89 (t, J=3.6 Hz, 2H), 1.88-1.29 (m, 2H); MS; 275 (M+H)$^+$.

Example: 4

5-Chloro-1-ethyl-3a,7a-dihydro-1H-indazole-3-carbonitrile (9)

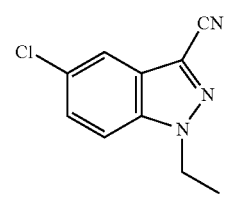

9

Potassium carbonate (0.28 g; 1.8 mmol) and ethyl bromide (0.2 mL; 1.8 mmol) were added to a suspension of 5-chloro-1H-indazole-3-carbonitrile 4 (0.12 g; 0.6 mmol) in acetone (10 mL). The reaction mixture was heated at 65° C. for 4 h, cooled and filtered. The filtrate was concentrated under reduced pressure and purified by column chromatography (silica gel 100-200 mesh, 2:8 Ethyl acetate: Pet ether) to afford 9 (0.13 g, 94%) as a pale yellow solid. $^1$H NMR (200 MHz, CDCl$_3$): δ=7.82 (t, J=1.1 Hz, 1H), 7.47 (s, 2H), 4.49 (d, J=7.2 Hz, 2H), 1.57 (t, J=7.3 Hz, 4H); MS; 206 (M+H)$^+$.

5-Chloro-3-(4,5-dihydro-1H-imidazol-2-yl)-1-ethyl-1H-indazole (10) NDS100282

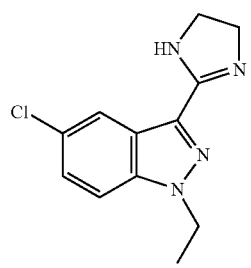

10

NDS-100282

A mixture of 9 (150 mg, 0.7 mmol), EDA (4 mL), and $P_2S_5$ (0.065 g, 0.3 mmol) was heated at 120° C. for 5 h. The reaction mixture was poured into ice solid was obtained, filtered through Buchner funnel washed with diethyl ether and dried under vacuum to afford (10) NDS100282 (0.11 g, 60%) as off white solid. $^1$H NMR (400 MHz, CD$_3$OD) δ=8.12 (s, 1H), 7.68 (d, J=9.0 Hz, 1H), 7.44 (dd, J=2.0, 9.0 Hz, 1H), 4.53 (q, J=7.3 Hz, 2H), 3.95 (s, 4H), 1.58-1.46 (m,

Example: 5

1-Benzyl-5-chloro-3a,7a-dihydro-1H-indazole-3-carbonitrile (11)

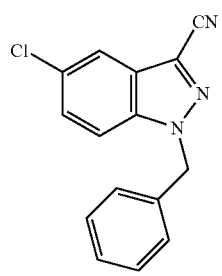

11

Potassium carbonate (0.35 g; 2.5 mmol) and benzyl bromide (0.3 mL; 2.5 mmol) were added to a suspension of 5-chloro-1H-indazole-3-carbonitrile 4 (0.15 g; 0.8 mmol) in acetone (10 mL). The reaction mixture was heated at 65° C. for 4 h, cooled and filtered. The filtrate was concentrated under reduced pressure and purified by column chromatography (silica gel 100-200 mesh, 2:8 Ethyl acetate: Pet ether) to afford (11) (0.18 g, 80%) as a pale yellow solid. $^1$H NMR (200 MHz, CDCl$_3$): δ=7.83 (t, J=1.2 Hz, 1H), 7.41-7.29 (m, 5H), 7.25-7.19 (m, 2H), 5.64 (s, 2H); MS; 268 (M+H)$^+$.

1-Benzyl-5-chloro-3-(4,5-dihydro-1H-imidazol-2-yl)-1H-indazole 12 (NDS100283)

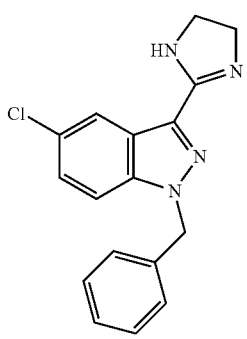

NDS-100283

1-Benzyl-5-chloro-3a,7a-dihydro-1H-indazole-3-carbonitrile 11 (160 mg, 0.6 mmol), EDA (4 mL), and P$_2$S$_5$ (0.053 g, 0.2 mmol) was heated at 120° C. for 5 h. The reaction mixture was poured into ice solid was obtained, filtered through Buchner funnel washed with diethyl ether and dried under vacuum to afford 12 (NDS100283) (0.100 g, 54%) as off white solid. $^1$H NMR (400 MHz, CD$_3$OD) δ=8.26-8.11 (m, 1H), 7.50 (d, J=8.8 Hz, 1H), 7.34 (dd, J=1.8, 8.9 Hz, 1H), 7.29-7.17 (m, 5H), 4.91 (s, 2H), 3.78 (s, 4H); $^{13}$C NMR (100 MHz, CD$_3$OD) δ=160.3, 139.1, 136.3, 134.2, 128.4, 127.9, 127.6, 127.2, 127.0, 122.9, 120.8, 111.2, 52.9, 48.9; MS 311 (M+H)$^+$.

31-1); $^{13}$C NMR (100 MHz, CD$_3$OD) δ=159.9, 138.8, 130.4, 128.7, 127.4, 122.4, 119.7, 111.5, 44.5, 13.6; MS; 249 (M+H)$^+$.

Example: 6

3-(4,5-dihydro-1H-imidazol-2-yl)-1H-indazole (16) NDS100277

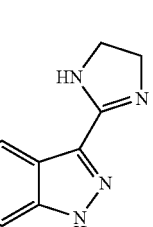

NDS-100277

Following the same procedure used for the synthesis of 5 (NDS100178). Yield: 51%; $^1$H NMR (200 MHz, DMSO-d$_6$) δ=8.25 (d, J=8.1 Hz, 1H), 7.67-7.55 (m, 1H), 7.48-7.35 (m, 1H), 7.23 (d, J=7.3 Hz, 1H), 3.66 (s, 4H); $^{13}$C NMR (50 MHz, DMSO-d$_6$) δ=159.8, 141.1, 135.8, 126.2, 122.0, 121.4, 121.1, 110.5, 49.4; MS 187 (M+H)$^+$.

1-Methyl-1H-indazole-3-carbonitrile 17

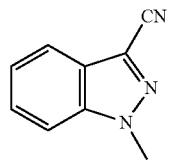

Following the procedure for the synthesis of 6. Yield: 97%; $^1$H NMR (200 MHz, CDCl$_3$) δ=7.84 (td, J=0.9, 8.2 Hz, 1H), 7.57-7.47 (m, 2H), 7.37 (dd, J=4.0, 8.0 Hz, 1H), 4.17 (s, 3H); MS 158 (M+H)$^+$.

Example: 7

3-(4,5-dihydro-1H-imidazol-2-yl)-1-methyl-1H-indazole 18 (NDS100278)

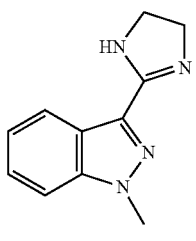

NDS100278

Following the same procedure for the synthesis of 7 (NDS100179). Yield: 42%; $^1$H NMR (200 MHz, CD$_3$OD) δ=8.16 (td, J=1.0, 8.2 Hz, 1H), 7.57 (td, J=0.9, 8.5 Hz, 1H), 7.44 (ddd, J=1.0, 6.9, 8.4 Hz, 1H), 7.37-7.20 (m, 1H), 4.22-4.06 (m, 3H), 3.78 (s, 4H); $^{13}$C NMR (100 MHz, CD$_3$OD) $\delta$=161.0, 141.1, 134.1, 126.6, 121.9, 121.8, 121.5, 109.3, 49.0, 34.8; MS 201 (M+H)$^+$.

Example: 8

3-(3a,4,5,6,7,7a-hexahydro-1H-benzo[d]imidazol-2-yl)-1H-indazole (19) NDS100281

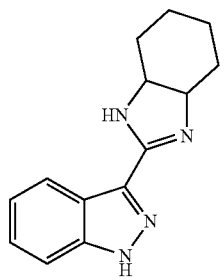

NDS-100279

Following the same procedure for the synthesis of 8. Yield: 30%; $^1$H NMR (200 MHz, CD$_3$OD) $\delta$=8.09 (d, J=8.1 Hz, 1H), 7.56-7.43 (m, 1H), 7.31 (s, 1H), 7.16 (d, J=7.8 Hz, 1H), 3.84 (t, J=3.6 Hz, 2H), 1.84-1.24 (m, 8H); $^{13}$C NMR (50 MHz, CD$_3$OD) $\delta$=162.1, 143.7, 135.9, 127.7, 123.3, 122.5, 122.2, 112.0, 60.5, 28.9, 21.8; MS 241 (M+H)$^+$.

Example 9

Measurement of Insulinotropic Activity of NDS100178 and NDS100179

Material and Methods

Insulinotropic activity of the NDS100178 and NDS100179 was measured by a well-optimized ELISA based Assay (Shantani Protocol #5205) described below.

Materials

MIN6Cell (source: National Center for Cell Sciences, Pune)
Mouse Insulin ELISA kit (Mercodia, 10-1247-01)
Plate Shaker (MixMatefromEppendorf)
HEPES Balanced Krebs-Ringer bicarbonate buffer (components as follows)

Method i. Seed proliferating culture of MIN-6 cells into a 6 well plate with almost half the confluency two days before the experiment.
ii. One the day of Insulin induction experiment, the cells should become almost confluent and are in good condition.
iii. On the day of experiment, first prepare 1×KRB-HEPES buffer with 0.1% BSA (for rinse) and without BSA (for equilibration and insulin induction) as described in the materials.
iv. Prepare equilibration buffer: 1×KRB-HEPES buffer without BSA containing 3.3 mM glucose (to bring down the glucose level of all cells to the same level). For example, add 66 ul 1 M glucose stock solution to 20 ml KRB-HEPES buffer without BSA.
v. Prepare the stimulating buffer (insulin induction): 1×KRB-HEPES buffer without BSA containing the defined glucose level (in most cases, it will be 16.7 mM glucose) and the desired concentration of molecule.
vi. Pre warm all the buffers to 37° C. in the water bath (at 15 minutes).
vii. Remove media from all wells, rinse each well twice with 2 ml KRB-HEPES buffer containing 0.1% BSA.
viii. Add 2 ml of equilibration buffer in each well and incubate at 37° C. for half an hour.
ix. After the incubation add 2 ml of stimulating buffer in respective wells (properly labelled) and incubate 37° C. for 1 hour.
x. In the meanwhile, turn on the refrigerated centrifuge and set the temperature to 4° C. Take out enzyme conjugate, diluent buffer, Calibrator 0 and stripes needed (for example, two stripes for 8 samples to be run in duplicate) from Mercodia ELISA kit box (store at 4° C.) and warm up them to RT.
xi. After the 1 hour incubation is over take out the plates form the incubator, do not disturb the cells and take out 1 ml of stimulating buffer in properly labelled precooled tubes.
xii. Centrifuge the tubes at 600 g for 5 min.
xiii. Take out 500 ul in fresh properly labelled precooled tubes.
xiv. Now dilute the samples 1:30 in calibrator 0 i.e. add 3 ul of each sample to 87 ul of Calibrator 0 in 8 different properly labelled 0.5 ml tubes. Mix them well.

| Components | Stock Conc. (mM) | mol wt. | amount required to prepare 50 ml stock | (1X) HEPES KR-Buffer (mM) | Volume of the stock require to prepare working soln (ml) | |
|---|---|---|---|---|---|---|
| | | | | | for 50 ml with 0.1% BSA | for 50 ml without BSA |
| NaCl | 5000 | 58.44 | 14.61 | 119 | 1.19 | 1.19 |
| KCl | 100 | 74.55 | 0.37 | 4.74 | 2.37 | 2.37 |
| CaCl2 | 100 | 110.98 | 0.55 | 2.54 | 1.27 | 1.27 |
| MgCl2 | 100 | 203.31 | 1.02 | 1.19 | 0.595 | 0.595 |
| KH2PO4 | 100 | 136.08 | 0.68 | 1.19 | 0.595 | 0.595 |
| NaHCO3 | 200 | 84.01 | 0.84 | 25 | 6.25 | 6.25 |
| HEPES | 1000 | 1M stock | 0.00 | 10 | 0.5 | 0.5 |
| Distilled Water | | | | | 37.23 | 37.23 |
| BSA | | | | 0.10% | 50 mg | No BSA |

*HEPES is 2-[4-(2-hydroxyethyl)piperazin-1-yl]ethanesulfonic acid xv. Prepare 1× enzyme conjugate buffer, i.e. mix 180 ul enzyme (11×) with 1800 ul diluent buffer for ELISA of two stripes.

xvi. Add 10 ul of each sample (diluted, in duplicate) in the two adjacent wells. Be careful not to touch the bottom.

xvii. Carefully add 100 ul of Enzyme Conjugate buffer (1×) to each well and incubate on a plate shaker (eppendorf MixMate) at 800 rpm for 2 hours at 25° C.

xviii. 45 min before the incubation is over take out wash buffer, substrate TMB and Stop solution. Keep them at RT.

xix. 5 min before the incubation is over prepare 1× wash buffer (21×), i.e. 40 ml distilled water+2 ml (21×) wash buffer in a reservoir.

xx. After the incubation is over, wash each well 7 times with 350 ul wash buffer. Use a multichannel (175 ul).

xxi. After the washing add 200 uL substrate TMB solution in each well. Maintain a proper pace.

xxii. Allow to incubate for 15 min. Set the program on the plate reader, to take absorbance read at 450 nm. Add a 5 sec shake step to allow proper mixing.

xxiii. After incubation immediately add 50 ul Stop solution in each well at same pace and take absorbance read at 450 nm.

Assay conditions were kept same in all the assays. The difference in absorption-value for control experiment (no treatment with molecule) over different days is attributed to cell culture conditions. Other varying conditions are specified in the respective graphs. Results obtained are compiled below.

[Note: If not mentioned specifically, HG=High Glucose (16.7 mM), LG=Low Glucose (3.3 mM)]

Results

NDS100178 and NDS100179 Enhances Glucose Stimulated Insulin Secretion

Insulin secretion ability of NDS100178 and NDS100179 was measured in three different days as in FIG. 1. As represented below significant increase in the insulin secretion from MIN6 cells in high glucose conditions was observed when the cells were treated with either NDS100178 or NDS100179, both at 33 uM concentration, for 1 hour.

Insulinotropic Activity of the NDS100178 and NDS100179 is Glucose Dependent

Figure 2:
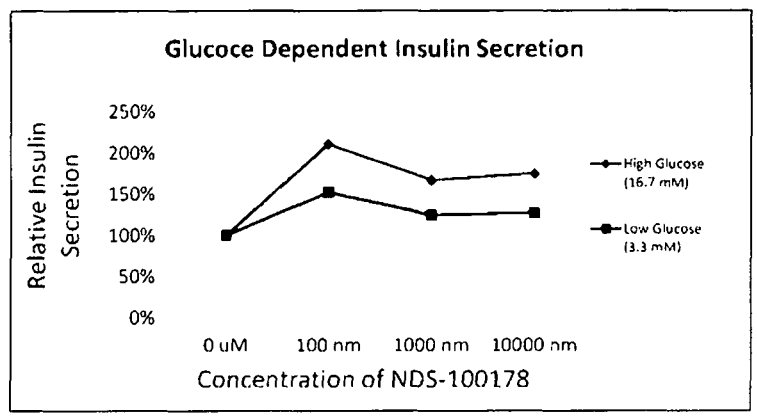
FIG. 2: depicts Glucose Dependent activity of NDS100178 and NDS100179.
Figure 2:
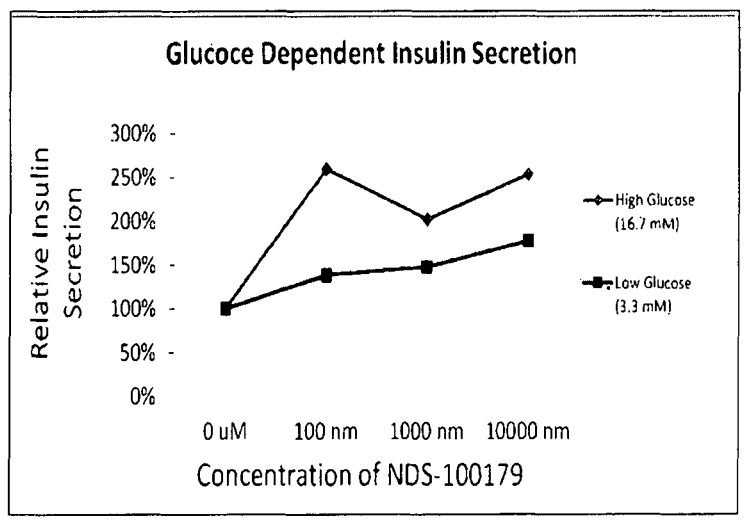
Figure 3:
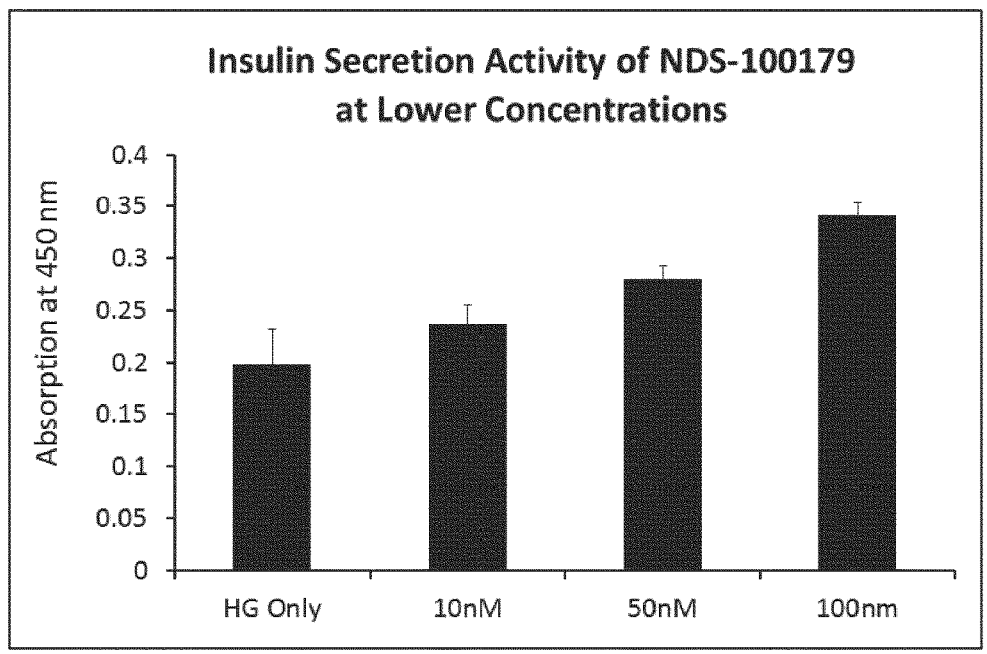
FIG. 3: depicts Insulinotropic Activity of NDS100178 and NDS100179 at Low Concentrations.
Figure 3:
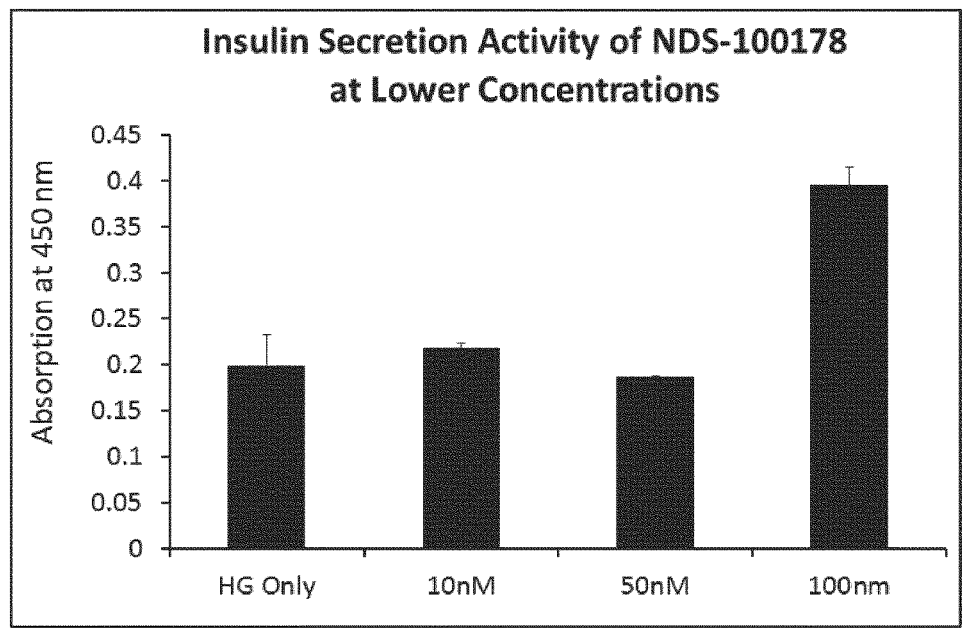

Insulinotropic activity of NDS100178 and NDS100179 was found to be glucose dependent. As represented below significant increase in insulin secretion was observed over the respective control where cells were present in high glucose condition compared to lower glucose conditions as in FIG. 2.

NDS100178 and NDS100179 Exhibit Insulinotropic Activity at Low Concentrations

As shown below NDS100178 induced more than 100% increase in insulin secretion when incubated at 100 nM concentration. No significant difference over the control experiments was obtained when concentration was reduced to 50 nM or 10 nM.

Interestingly NDS100179 was active even at as low as 10 nM concentration. Although the increase in insulin secretion over the control experiment in presence of 10 nM NDS100179 was not found to be statistically significant, incubation with 50 nM and 100 nM concentration of the molecule clearly showed the trend that molecule was an active insulinotrope.

Insulinotropic Properties of the Compounds

Insulin Secretion from MIN6 Cells Table 1:

| Compound | Concentration (μM) | Insulin Secretion (ng/ml) |
|---|---|---|
| NDS100178 | 10.0/1.0/0.1 | 35.09 (4.0)/12.49 (1.9)/8.91 (1.6) |
| NDS100179 | 10.0/1.0/0.1 | 15.45 (1.2)/10.27 (0.6)/5.55 (1.0) |
| NDS100277 | 10.0/1.0/0.1 | 20.96 (1.7)/14.66 (0.4)/11.87 (0.8) |
| NDS100278 | 10.0/1.0/0.1 | 13.16 (1.6)/10.80 (0.2)/12.43 (1.1) |
| NDS100279 | 10.0/1.0/0.1 | 21.45 (0.9)/14.57 (3.0)/10.45 (1.6) |
| NDS100281 | 10.0/1.0/0.1 | 20.85 (0.8)/16.91 (0.1)/14.73 (0.5) |
| NDS100282 | 10.0/1.0/0.1 | 33.15 (0.7)/18.73 (1.0)/13.02 (0.3) |
| NDS100283 | 10.0/1.0/0.1 | 50.45 (3.8)/20.08 (0.8)/11.35 (1.0) |
| Example-6 of Patent US20040009976 Compound: 5-Chloro-2-methyl-3-(4,5-dihydro-1-H-imidazol-2-yl)-1H-indole | 1.0/0.1 | 3.68 (2.11)/1.39 (0.15) |

Values in bracket are standard error of the measurements.

Example 10

Glucose Reduction and Glucose Dependent Insulin Secretion in Non-Diabetic Laboratory Mice by NDS100179

Figure 4:
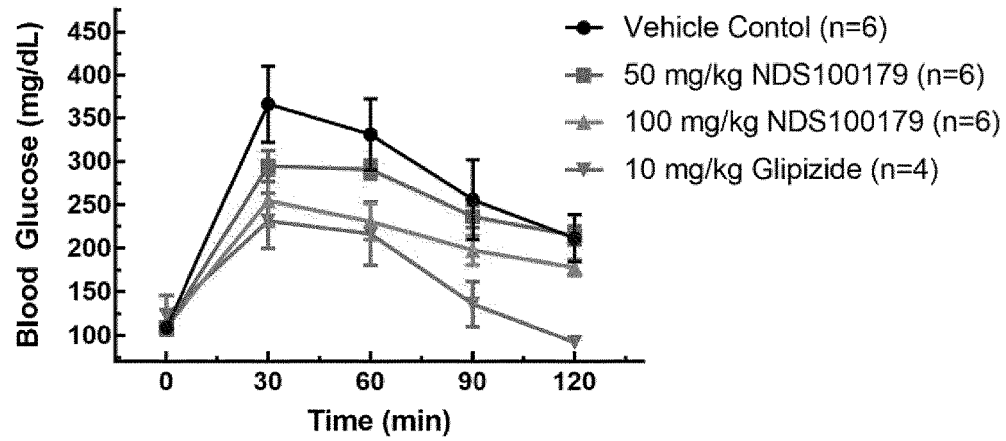
FIG. 4: depicts a) Oral Glucose Tolerance Test: Reduction of plasma glucose in presence of NDS100179 in C57BL Mice b) Oral Glucose Tolerance Test: NDS100179 Dose' dependent % Change in Total AUC (Glucose) in C57BL Mice.
Figure 4:
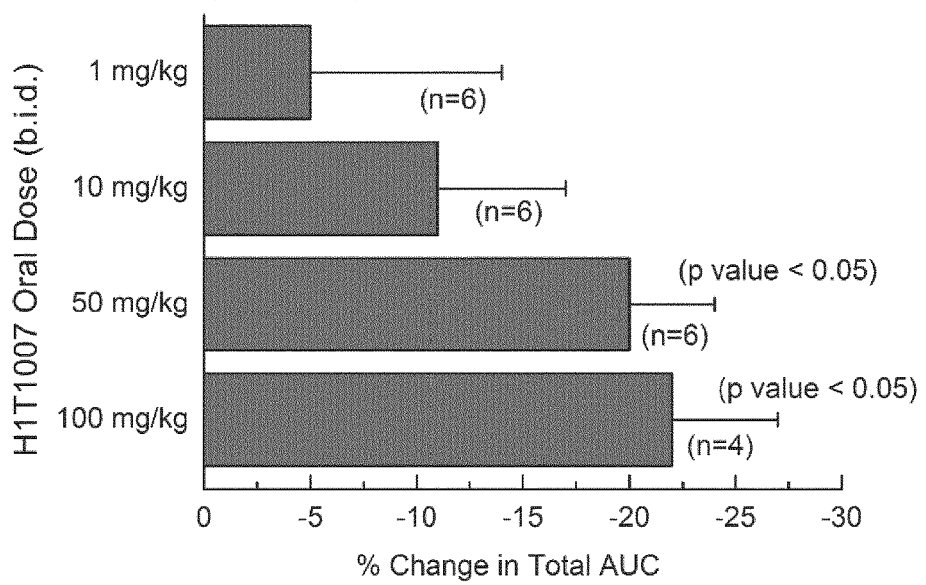

Glucose Reduction in C57BL/6J Mice 12-13 weeks male C57BL/6J mice were fasted overnight. In the morning animals were orally dosed with different concentrations of NDS100179 or control vehicle along with 3 g/kg of glucose. Blood glucose was measured just before the dose and then 30, 60 90 and 120 minutes after the compound dose. Molecule dose dependently reduce the blood glucose in C57Bl/6J mice (FIG. 4).

Insulin Increase in C57BL/6J Mice

Figure 5:
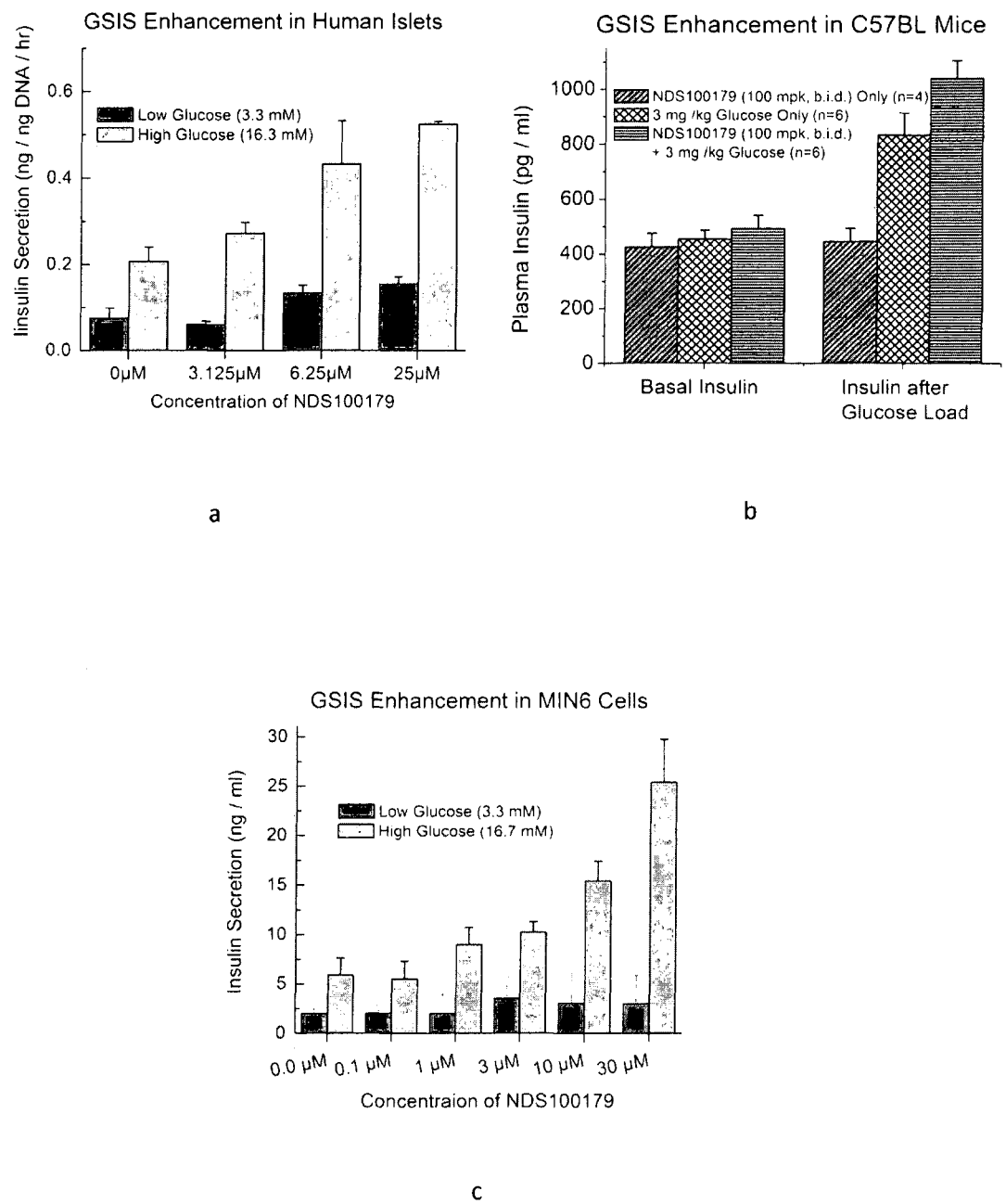
FIG. 5: depicts a) GSIS enhancement in human Islets; b) GSIS enhancement in C57BL Mice; c) GSIS enhancement in MIN6 cells.

Insulin at 0 and 15 minutes time points was also measured in the studies conducted above where 12-13 weeks male C57BL/6J mice were fasted overnight and in the morning orally dosed with different concentrations of NDS100179 or control vehicle along with 3 g/kg of glucose. Insulin secretion from NDS100179 was found to be blood plasma concentration glucose dependent (FIG. 5).

Example 11

Enhancement of Glucose Stimulated Insulin Secretion (GSIS) by NDS100179

NDS100179 are insulinotropic compounds that enhance insulin secretion only at high glucose concentration. NDS100179 induced insulin measurements at low and high glucose condition were carried out in Human Islets, Mice and MIN6 cells. Data presented clearly shows that GSIS enhancement capability of NDS100179 is similar in different biological systems (FIG. 5).

Example 12

NDS100179—Fasted Plasma Glucose and Glucose Tolerance in Animal Model of Diabetes (Db/Db Mice)

db/db or leptin null mice are well accepted model of diabetes. 7 week old db/db mice were dosed orally with 10 mg/kg, 30 mg/kg of NDS100179 and vehicle alone for 30 days. Fasted plasma glucose levels in the animals were measured before the start of the study, at day 15 and day 30. Animals treated with the NDS100179 showed significant control in rise of basal glucose level, an effect that was dependent on the amount of molecule given to the animals. Animals treated with 30 mg/kg of NDS100179 showed no statistically significant rise in fasted blood glucose levels. Oral Glucose Tolerance Test (OGTT) performed at the end of 30 days showed significant improvement in glucose tolerance in NDS100179 treated mice (FIGS. 6a and 6b).

Example 13

NDS100179—Beta-Cell Function Preservation/Restoration in Animal Model of Diabetes (Db/Db Mice)

7 week db/db mice were dosed orally with 10 mg/kg, 30 mg/kg of NDS100179 and vehicle alone for 30 days. Beta-cell functionality was assessed using HOMA-beta % calculations at the end of 30 days. NDS100179 treated mice showed significant improvements in beta-cell functions (FIG. 6c).

Example 14

NDS100179—Reduction in Triglyceride in Animal Model of Diabetes (Db/Db Mice)

7 week db/db mice were dosed orally with 10 mg/kg, 30 mg/kg of NDS100179 and vehicle alone for 30 days. Triglyceride levels were measured at the end of 30 days. NDS100179 treated mice showed significant reduction in triglyceride levels (FIG. 7a).

Example 15

NDS100179—No Body Weight Alteration in Animal Model of Diabetes (Db/Db Mice)

7 week db/db mice were dosed orally with 10 mg/kg, 30 mg/kg of NDS100179 and vehicle alone for 30 days. Animal body weight was measured every third day. No significant change in body weight was observed in NDS100179 treated mice (FIG. 7b).

Example 16

Pharmacokinetic Properties of NDS100179

Figure 9:
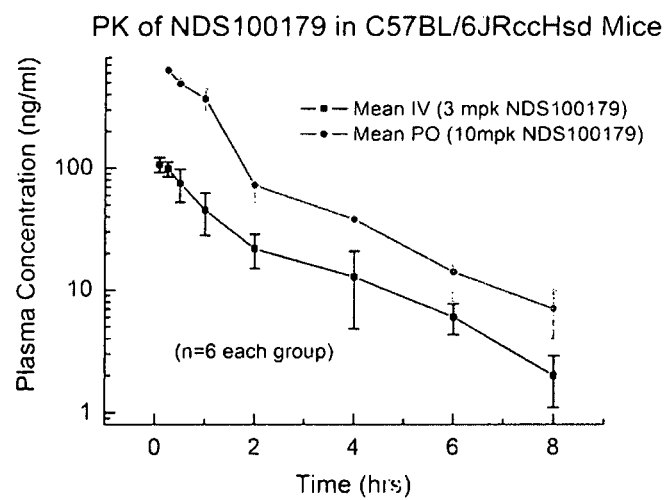
FIG. 9: depicts PK of NDS100179 in C57BL/6JRccHsd Mice.
Figure 10:
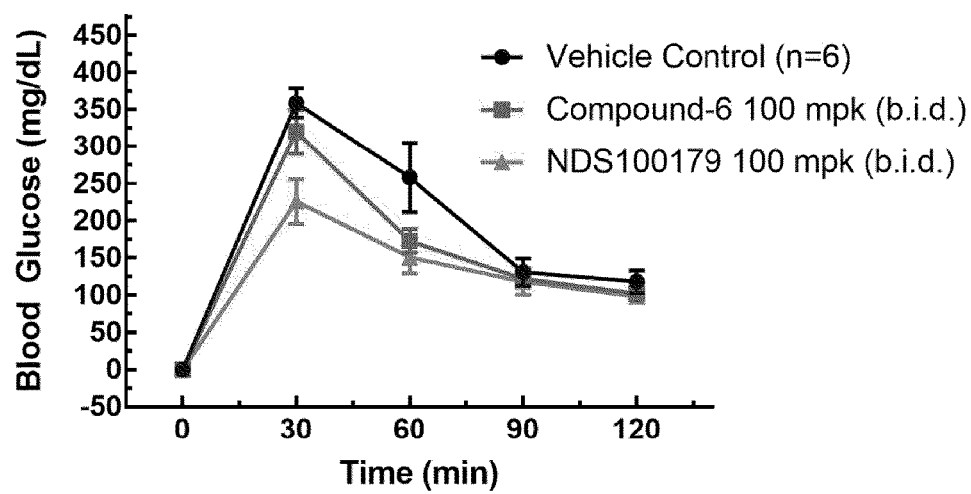
FIG. 10: depicts Oral Glucose Tolerance Test in C57BL/6JRccHsd Mice.

Based on the pharmacokinetics studies performed in Mice NDS100179 is 100% orally bioavailable compound (FIG. 9).

| Measurements | Values |
|---|---|
| Cmax (ng/ml) | 631.1 |
| Tmax (h) | 0.25 |
| AUC(inf) (hr*ng/ml) | 854.231 |
| AUC(0-t) (hr*ng/ml) | 837.113 |
| AUC(inf)/AUC(0-t) % | 102.049 |
| t½ (h) | 1.7 |

Example 17

In-Vitro ADME Properties

| Compound | Mean Kinetic Solubility (μM) | CYP3A4 Inhibition | Metabolic Study MLM Mean % PCR* | Metabolic Study HLM Mean % PCR* | Intrinsic Clearnace MLM (μl/min/mg of protein) |
|---|---|---|---|---|---|
| NDS100178 | 214.20 | No inhibition Seen | 38.84 | 79.70 | 80.8 |
| NDS100179 | 205.27 | No inhibition Seen | 39.25 | 80.11 | 63.7 |
| NDS100282 | 201.60 | IC50 > 10 uM | 33.27 | 71.71 | 56.4 |
| NDS100283 | 113.39 | No inhibition Seen | 19.09 | 86.02 | 145.5 |
| Example-6 of Patent US20040009976 Compound: 5-Chloro-2-methyl-3-(4,5-dihydro-1-H-imidazol-2-yl)-1H-indole | 196.50 | No inhibition Seen | 64.83 | 99.11 | 21.3 |

Example 18

NDS100179—Increase in Glucose Uptake in HepG2 Cells

NDS100179 increase glucose uptake in HepG2 cells (FIG. 8). The assay was performed after making the HepG2 cells insulin resistant by culturing them in high glucose condition with respective drugs for 24 hours. The assay was performed after 24 hours by allowing the cells to starve for 2 hrs in serum free media (containing respective drug) followed by 30 min incubation in KRB buffer (with respective drugs) and lastly incubating with 2-NBDG (fluorescent glucose analgoue) for 15 min. The cells were thoroughly washed and lysed with 1% triton-X. The fluorescence reading was immediately taken at Ex:465 and Em:5.40.

Example 19

Mechanism of Action

NDS100178 series of compound primarily activates imidazoline receptor 11/13 (1050~50 nM). In high glucose condition this activation leads to formation of Diacylglycerol (DAG). DAG subsequently generates Arachidonic Acids (AA) in the cell. Metabolites of AA especially epoxyeicosatrienenoic acids (EETs) and hydroxyeicosatetrenoic acids (HETEs) induce exocytosis leading to increased secretion of insulin from the cells. The other major signalling pathway that can alter the glucose/DAG induced AA pool is the leukotriene pathway, that, by metabolizing AA into different leukotrienes and not EET and HETE can suppress its insulin secretion effect. Molecules that can inhibit metabolism of AA through leukotriene pathway can maintain AA pool leading to its metabolism only through EETs and HETEs and thus can enhance increase insulin secretion. One of the major enzymes in leukotriene pathway is LTA4H hydrolase that converts LTA4 into LTB4, a AA derivative that suppresses insulin secretion. A novel finding that inhibiting LTA4H can enhance insulin secretion has been established by the inventors. NDS100178 inhibits LTA4H (IC50<500 nM) while the IC50 against LTA4H target of compound 6 from patent US20040009976 Compound: 5-Chloro-2-methyl-3-(4,5-dihydro-1-H-imidazol-2-yl)-1H-indole) is above 10 uM.

ADVANTAGES OF THE INVENTION

New anti-diabetic compounds.
Controlled Secretion of Insulin with respect to glucose level in the surrounding environment.
Ameliorates any side effects of other antidiabetic drugs like hypoglycemia.
Provides Cardiovascular Protection by decreasing triglycerides
Enhances/Preserves beta-cell functionality
Effective against both type 1 and type 2 diabetes and related complications.
Process of preparation economical and commercially feasible.

The invention claimed is:

1. An indazole compound of formula 1,

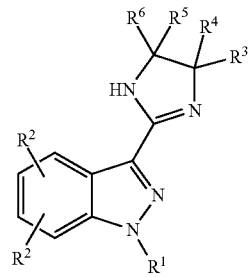

Formula 1 wherein:
$R^1$ is hydrogen or alkyl or aryl or heteroaryl;
$R^2$ at each occurrence is independently selected from H or halogen
$R^3$, $R^4$, $R^5$, and $R^6$ are independently hydrogen or alkyl, aryl, or hetero aryl; or
any two adjacent groups selected from $R^3$, $R^4$, $R^5$, and $R^6$ form a 3-8 membered cyclic ring which may additionally contain hetero atoms selected from oxygen or nitrogen; and
pharmaceutically acceptable salt thereof.

2. The indazole compound of claim 1 selected from the group consisting of
   (i) 5-Chloro-3-(4,5-dihydro-1H-imidazol-2-yl)-1H-indazole;
   iii) 5-Chloro-3-(4,5-dihydro-1H-imidazol-2-yl)-1-methyl-3a,7a-dihydro-1H-indazole;
   (iii) 5-chloro-3-(3a,4,5,6,7,7a-hexahydro-1H-benzo[d]imidazol-2-yl)-1H-indazole;
   (iv) 5-Chloro-3-(4,5-dihydro-1H-imidazol-2-yl)-1-ethyl-1H-indazole;
   (v) 1-Benzyl-5-chloro-3-(4,5-dihydro-1H-imidazol-2-yl)-1H-indazole;
   (vi) 3-(4,5-dihydro-1H-imidazol-2-yl)-1H-indazole;
   (vii) 3-(4,5-dihydro-1H-imidazol-2-yl)-1-methyl-1H-indazole;
   (viii) 3-(3a,4,5,6,7,7a-hexahydro-1H-benzo[d]imidazol-2-yl)-1H-indazole.

3. A process for the preparation of the compound of claim 1, comprising the steps of;
   (i) converting 5-Chloro isatin into 5-chloro indazole 3-carboxylic acid;
   (ii) treating 5 chloro indazole 3-carboxylic acid with isobutyl chloroformate and N-methylmorpholine under argon followed by reaction with aq. ammonia to obtain 5-chloro-1H-indazole-3-carboxamide;
   (iii) treating 5-chloro-1H-indazole-3-carboxamide with pyridine and trifluroacetic anhydride to obtain the corresponding cyano compound;
   (iv) reacting the corresponding cyano compound with potassium carbonate and alkyl halide in acetone solvent to obtain substituted indazole carbonitrile;
   (v) reacting the substituted indazole carbonitrile with diamine in the presence of $P_2S_5$ to obtain the compound of formula 1.

4. The process of claim 3, wherein the alkyl halide used in step (iv) is selected from the group consisting of ethyl bromide, methyl iodide, and benzyl bromide.

5. The process of claim 3, wherein the diamine used in step (v) is selected from the group consisting of 1,2-cyclohexanediamine, and ethylene diamine.

6. A pharmaceutical formulation comprising the compound of claim 1 and one or more pharmaceutically acceptable carriers, diluents or excipients.

7. A method of treating a disease in a subject, comprising administration to the subject a therapeutically effective amount of the indazole of claim 1, wherein the disease is selected from the group consisting of diabetes, diabetic complications, metabolic disorders, cardiovascular dysfunctions, and diseases characterized by impaired glucose metabolism, altered triglyceride levels or reduced beta-cell functions.

* * * * *